United States Patent
Shinkawa et al.

(10) Patent No.: US 10,626,405 B2
(45) Date of Patent: *Apr. 21, 2020

(54) BASE SEQUENCE FOR PROTEIN EXPRESSION AND METHOD FOR PRODUCING PROTEIN USING SAME

(71) Applicant: HONDA MOTOR CO., LTD., Minato-Ku, Tokyo (JP)

(72) Inventors: Satoru Shinkawa, Saitama (JP); Shigenobu Mitsuzawa, Saitama (JP); Maiko Tanaka, Saitama (JP); Masayuki Machida, Hokkaido (JP); Hiroko Hagiwara, Ibaraki (JP); Hideaki Koike, Ibaraki (JP); Mahoko Kuninaga, Ibaraki (JP)

(73) Assignee: Honda Motor Co., Ltd., Tokyo (JP)

( * ) Notice: Subject to any disclaimer, the term of this patent is extended or adjusted under 35 U.S.C. 154(b) by 60 days.

This patent is subject to a terminal disclaimer.

(21) Appl. No.: 15/745,030

(22) PCT Filed: Jul. 15, 2016

(86) PCT No.: PCT/JP2016/003359
§ 371 (c)(1),
(2) Date: Jan. 15, 2018

(87) PCT Pub. No.: WO2017/010107
PCT Pub. Date: Jan. 19, 2017

(65) Prior Publication Data
US 2018/0208936 A1 Jul. 26, 2018

(30) Foreign Application Priority Data
Jul. 16, 2015 (JP) .................... 2015-142214

(51) Int. Cl.
| | | |
|---|---|---|
| C12N 15/63 | (2006.01) | |
| C12N 15/80 | (2006.01) | |
| C12N 15/62 | (2006.01) | |
| C07K 14/38 | (2006.01) | |
| C12N 15/82 | (2006.01) | |
| C12P 21/02 | (2006.01) | |

(52) U.S. Cl.
CPC .......... *C12N 15/8226* (2013.01); *C07K 14/38* (2013.01); *C12N 15/62* (2013.01); *C12N 15/63* (2013.01); *C12N 15/80* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 2013/0196374 A1 | 8/2013 | Koishihara | |
| 2018/0208934 A1* | 7/2018 | Shinkawa | ............... C12N 15/63 |

FOREIGN PATENT DOCUMENTS

| | | |
|---|---|---|
| EP | 0 238 023 A2 | 9/1987 |
| JP | 3343567 B2 | 11/2002 |
| JP | 2012-075369 A | 4/2012 |
| WO | 98/01470 A1 | 1/1998 |

OTHER PUBLICATIONS

Marui et al., "Kojic acid biosynthesis in Aspergillus oryzae is regulated by a Zn (II) (2) Cys (6) transcriptional activator and induced by kojic acid at the transcriptional level", Journal of Bioscience and Bioengineering, Jul. 2011, vol. 112, No. 1, pp. 40-43.

Tsuboi et al., "Improvement of the Aspergillus oryzae Enolase Promoter (P-enoA) by the Introduction of cis-Element Repeats", Bioscience, Biotechnology, and Biochemistry, Jan. 2005, vol. 69, No. 1, pp. 206-208.

Gomi et al., "Molecular Cloning and Characterization of a Transcriptional Activator Gene, amyR, Involved in the Amylolytic Gene Expression in Aspergillus oryzae", Bioscience Biotechnology Biochemistry, Japan Society for Bioscience, Biotechnology, and Agrochemistry, Tokyo, Japan, Apr. 1, 2000, vol. 64, No. 4, pp. 816-827.

MacPherson et al., "A Fungal Family of Transcriptional Regulators: the Zinc Cluster Proteins", Microbiology and Molecular Biology Reviews: MMBR Sep. 2006, vol. 70, No. 3, pp. 583-604.

Tsukagoshi et al., "Regulation of the amylolytic and (hemi-)cellulolytic genes in aspergilli", Journal of General and Applied Microbiology, Feb. 2001, vol. 47, No. 1, pp. 1-19.

Terabayashi et al., "Identification and characterization of genes responsible for biosynthesis of kojic acid, an industrially important compound from Aspergillus oryzae", Fungal Genetics and Biology, San Diego, CA, US, Dec. 1, 2010, vol. 47, No. 12, pp. 953-961.

* cited by examiner

*Primary Examiner* — Channing S Mahatan
(74) *Attorney, Agent, or Firm* — Carrier Blackman & Associates, P.C.; William D. Blackman; Joseph P. Carrier

(57) ABSTRACT

To provide a base sequence for protein expression that can increase the yield of protein such as diastatic enzyme by further activating a promoter of a particular gene. A base sequence 1 for protein expression includes: a gene 3 encoding protein 2; a promoter 4 of the gene 3, the promoter being linked upstream of the gene 3; and a cis element 5 whose activity is improved by an artificial transcription factor 6, the cis element being linked further upstream of the promoter 4. The cis element 5 is represented by SEQ ID NO: 1.

11 Claims, 3 Drawing Sheets

Specification includes a Sequence Listing.

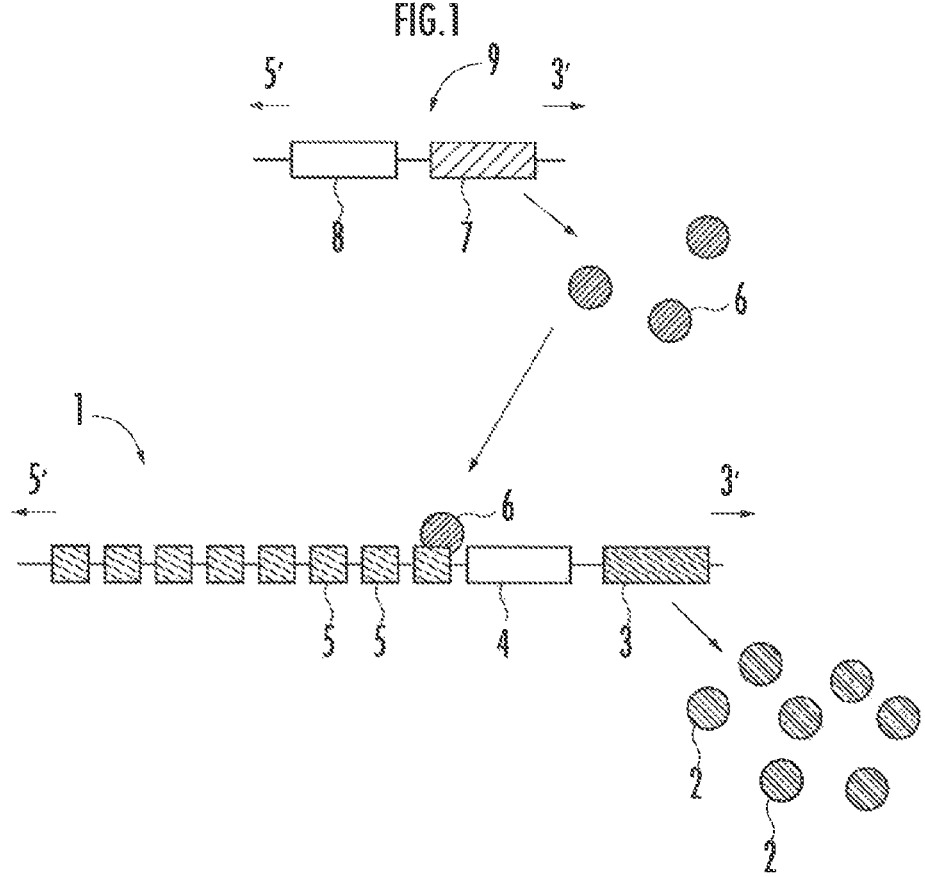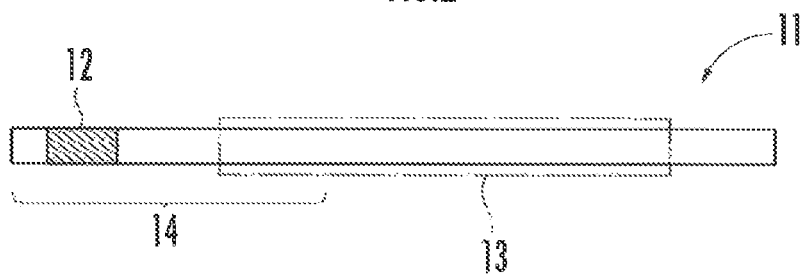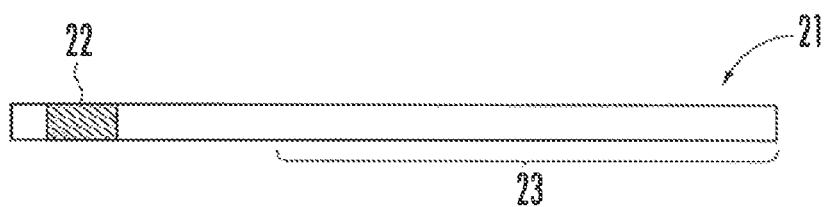

BASE SEQUENCE FOR PROTEIN EXPRESSION AND METHOD FOR PRODUCING PROTEIN USING SAME

TECHNICAL FIELD

The present invention relates to a base sequence for protein expression for use in the production of protein such as diastatic enzyme using koji mold, and a method for producing protein using the same.

BACKGROUND ART

Heretofore, it has been known that a base sequence for protein expression in which a cis element consisting of a particular base sequence is linked to a promoter of a particular gene that yields protein, when producing protein such as a diastatic enzyme using koji mold (see e.g., Patent Literatures 1 and 2). The conventional base sequence for protein expression can improve the activity of the promoter and can increase the yield of the protein, by linking the cis element to the promoter.

For example, Patent Literature 1 describes a technique of using enhancer DNA consisting of a XlnR/Ace2 binding sequence and a Hap complex binding sequence as a cis element and linking 12 cis elements upstream (on the 5'-terminal side) of a promoter of tef1 gene. According to Patent Literature 1, in this way, GUS activity by the promoter is reported to be improved approximately 4.9 times under solid culture conditions with wheat bran as a carbon source.

Also, Patent Literature 2 describes a technique of using enhancer DNA located at a promoter of α-glucosidase gene of koji mold (*Aspergillus oryzae*) as a cis element and linking 12 such cis elements upstream (on the 5'-terminal side) of the promoter. According to Patent Literature 2, in this way, GUS activity by the promoter is reported to be improved approximately 6 times under culture conditions with starch as a carbon source.

CITATION LIST

Patent Literature

[PTL 1]
Japanese Patent Application Laid-Open No. 2012-75369
[PTL 2]
Japanese Patent No. 3343567

SUMMARY OF INVENTION

Technical Problem

However, the conventional base sequence for protein expression merely links a cis element consisting of a particular base sequence to a promoter of a particular gene and is thus desired to be further modified.

In light of these circumstances, an object of the present invention is to provide a base sequence for protein expression that can increase the yield of protein such as diastatic enzyme by further activating a promoter of a particular gene, and a method for producing protein using the same.

Solution to Problem

In order to attain the object, the base sequence for protein expression of the present invention is a base sequence for protein expression comprising: a gene encoding protein; a promoter of the gene, the promoter being linked upstream of the gene; and a cis element whose activity is improved by an artificial transcription factor, the cis element being linked further upstream of the promoter, wherein the cis element is represented by SEQ ID NO: 1, and wherein the artificial transcription factor comprises a DNA binding domain comprising a base sequence of upstream 1 to 118 aa of a transcription factor KojR and an active domain comprising a base sequence of downstream 150 to 604 aa of a transcription factor AmyR, and the active domain is linked downstream of the DNA binding domain, and is represented by SEQ ID NO: 2.

According to the base sequence for protein expression of the present invention, the activity of the cis element represented by SEQ ID NO: 1 linked upstream of the promoter can be improved by the artificial transcription factor represented by SEQ ID NO: 2, and the activity of the promoter can be further improved by the cis element whose activity has been improved. As a result, the activity of the gene is improved by the promoter whose activity has been improved, so that the yield of the protein encoded by the gene can be increased.

The base sequence for protein expression of the present invention preferably comprises a base sequence for artificial transcription factor expression comprising: a gene encoding the artificial transcription factor represented by SEQ ID NO: 2; and a promoter of the gene, the promoter being linked upstream of the gene. According to the base sequence for artificial transcription factor expression, the activity of the gene encoding the artificial transcription factor represented by SEQ ID NO: 2 is improved by the promoter of the gene so that the artificial transcription factor encoded by the gene is produced.

For the base sequence for protein expression of the present invention, it is required that at least one cis element represented by SEQ ID NO: 1 should be linked upstream of the promoter. Preferably, the cis element is linked, for example, at any number in a range of 1 to 10, upstream of the promoter.

The expression vector of the present invention comprises the base sequence for protein expression of the present invention. According to the expression vector of the present invention, a transformant comprising the base sequence for protein expression of the present invention can be produced.

The transformant of the present invention comprises the base sequence for protein expression of the present invention. According to the transformant of the present invention, the yield of the protein encoded by the gene can be increased.

For the transformant of the present invention, it is preferred that koji mold should be used as a host cell, and it is more preferred that the koji mold should be an *Aspergillus oryzae* HO2 strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NITE BP-01750), or an *Aspergillus oryzae* HO4 strain (National Institute of Technology and Evaluation, Patent Microorganisms Depositary, #122, 2-5-8 Kazusakamatari, Kisarazu-shi, Chiba, Japan, Deposition Date: Dec. 9, 2014, Deposition No.: NITE BP-01980).

The method for producing a protein according to the present invention comprises culturing a transformant comprising the base sequence for protein expression of the present invention, and recovering the protein encoded by the gene overexpressed by the base sequence for protein expression, from the medium or the inside of the transformant after the culture.

The base sequence for protein expression of the present invention can increase the yield of the protein encoded by the gene, as mentioned above. Accordingly, when the transformant comprising the base sequence for protein expression of the present invention is cultured, the produced protein accumulates in the medium or the transformant after the culture. Therefore, the protein can be recovered.

BRIEF DESCRIPTION OF DRAWINGS

FIG. 1 is an illustrative diagram schematically showing the configuration and effect of a base sequence for protein expression of the present invention.

FIG. 2 is an illustrative diagram schematically showing a predicted structure of a transcription factor KojR.

FIG. 3 is an illustrative diagram schematically showing a predicted structure of a transcription factor AmyR.

DESCRIPTION OF EMBODIMENTS

Figure 4:
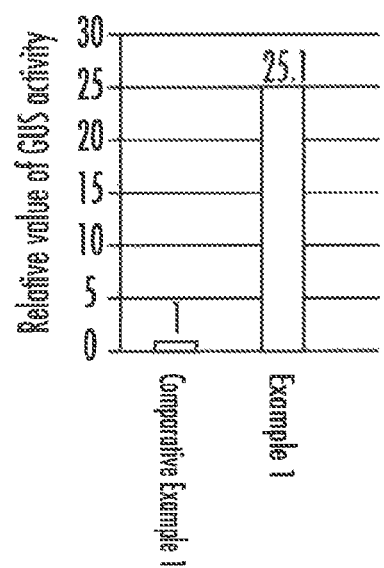
FIG. 4 is a graph showing a relative value of GUS activity when a transformant of the present invention was cultured for 60 hours with dextrin as a substrate.

Next, the embodiments of the present invention will be described further specifically with reference to the attached drawings.

As shown in FIG. 1, a base sequence 1 for protein expression of the present embodiment comprises: a protein gene 3 encoding a desired protein 2; a promoter 4 linked upstream (on the 5'-terminal side) of the protein gene 3; and a cis element 5 linked upstream (on the 5'-terminal side) of the promoter 4.

The protein 2 is, for example, a diastatic enzyme. The protein gene 3 may be any gene which encodes the protein 2.

The cis element 5 is composed of a base sequence comprising enhancer DNA located at a promoter of kojT gene, and the base sequence is gacggaaaagtcgggtagat (SEQ ID NO: 1). In the base sequence 1 for protein expression, 1 to 10, for example, 8 cis elements 5 are linked upstream of the promoter 4.

The base sequence 1 for protein expression also comprises a base sequence 9 for artificial transcription factor expression comprising: an artificial transcription factor gene 7 encoding an artificial transcription factor 6; and a promoter 8 linked upstream (on the 5'-terminal side) of the artificial transcription factor gene 7. The activity of the cis element 5 is improved by the artificial transcription factor 6.

The artificial transcription factor 6 is prepared from a transcription factor KojR 11 shown in FIG. 2 and a transcription factor AmyR 21 shown in FIG. 3. The transcription factors KojR 11 and AmyR 21 are transcription factors both classified into Cys6 cysteine-Zinc cluster type, among transcription factors having a zinc-coordinating DNA binding domain (Zn_Cluster).

As shown in FIG. 2, the transcription factor KojR 11 comprises upstream (5'-terminal side) Zn_Cluster 12 and comprises downstream (3'-terminal side) MHR 13 which is a highly homologous region common in transcription factors classified in Cys6 cysteine-Zinc cluster type. In this context, the transcription factor KojR 11 is composed of a base sequence of 555 aa in full length. The Zn_Cluster 12 is composed of a base sequence of 15 to 45 aa. The MHR 13 is composed of a base sequence of 148 to 281 aa.

In the transcription factor KojR 11, a DNA binding domain associated with binding to the cis element 5 is predicted to reside in a region 14 comprising the upstream Zn_Cluster 12. Examples of a candidate region of the DNA binding domain can include a region composed of a base sequence of 1 to 118 aa, a region composed of a base sequence of 1 to 195 aa, and a region composed of a base sequence of 1 to 239 aa.

On the other hand, as shown in FIG. 3, the transcription factor AmyR 21 comprises upstream (5'-terminal side) Zn_Cluster 22 and comprises a downstream (3'-terminal side) region 23 comprising an active domain. In this context, the transcription factor AmyR 21 is composed of a base sequence of 604 aa in full length. The Zn_Cluster 22 is composed of a base sequence of 13 to 52 aa.

Examples of a candidate region of the active domain in the transcription factor AmyR 21 can include a region composed of a base sequence of 113 to 604 aa, a region composed of a base sequence of 150 to 604 aa, a region composed of base sequence of 219 to 604 aa, and a region composed of a base sequence of 257 to 604 aa.

Accordingly, the artificial transcription factor of the present embodiment has a configuration (SEQ ID NO: 2) in which an active domain comprising a base sequence of downstream 150 to 604 aa of the transcription factor AmyR is linked downstream of a DNA binding domain comprising a base sequence of upstream 1 to 118 aa of the transcription factor KojR.

According to the base sequence 1 for protein expression of the present embodiment, as shown in FIG. 1, the artificial transcription factor 6 encoded by the artificial transcription factor gene 7 whose activity has been improved by the promoter 8 in the base sequence 9 for artificial transcription factor expression is produced, and the produced artificial transcription factor 6 binds to the cis element 5. The activity of the cis element 5 is improved by the binding to the artificial transcription factor 6. The activity of the promoter 4 is improved by the cis element 5 whose activity has been improved.

Then, the activity of the protein gene 3 is improved by the promoter 4 whose activity has been improved, so that the protein 2 encoded by the protein gene 3 whose activity has been improved, is produced. As a result, the base sequence 1 for protein expression of the present embodiment can increase the yield of the protein 2.

Next, Examples of the present invention will be shown.

EXAMPLE 1

(Construction of Transformant Introduced with Artificial Transcription Factor Gene (1))

In this Example, first, the genomic DNA gene of an *Aspergillus oryzae* HO2 strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NITE BP-01750) was used as a template in PCR to amplify an upstream sequence of tppA gene using primers 1 and 2, its downstream sequence using primers 3 and 4, a tef1 promoter gene using primers 5 and 6, an agdA terminator gene using primers 7 and 8, and a gene fragment for marker recycling using primers 9 and 10, while the genomic DNA gene of an *Aspergillus awamori* HA1 strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NITE BP-01751) was used as a template in PCR to amplify a gene cassette for pyrG gene expression using primers 11 and 12. DNA polymerase (manufactured by Toyobo Co., Ltd., product name: KOD FX neo) was used in each PCR amplification. The amplification products were each purified using a purification kit (manufactured by Qiagen N.V., product name: QIAquick PCR purification kit) to obtain a total of 6 gene fragments.

Next, an *E. coli*-derived plasmid pMD20 (manufactured by Takara Bio Inc.) was used as a template in PCR to amplify a gene fragment derived from the plasmid using primers 13 and 14 and the DNA polymerase. The amplification product was purified using the purification kit to obtain the gene fragment.

Next, these 7 gene fragments were sequentially treated with a cloning kit (manufactured by Takara Bio Inc., product name: In-Fusion HD Cloning kit) and used in the transformation of an *E. coli* HST08 strain (manufactured by Takara Bio Inc.) to construct a plasmid pPT.

Next, the plasmid pPT was treated with a restriction enzyme SmaI (manufactured by Takara Bio Inc.) at 30° C. and purified using the purification kit to obtain the restriction treatment product of the plasmid (gene fragment).

Next, the genomic DNA gene of an *Aspergillus oryzae* HO2 strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NILE BP-01750) was used as a template in PCR to amplify a DNA binding domain of a transcription factor KojR using primers 15 and 16 and an active domain of a transcription factor AmyR using primers 17 and 18. The DNA polymerase was used in each PCR amplification. The amplification products were each purified using the purification kit to obtain the DNA binding domain and the active domain.

Next, the DNA binding domain and the active domain were treated with the cloning kit and used in the transformation of an *E. coli* HST08 strain to construct a plasmid carrying an artificial transcription factor gene in which the DNA binding domain and the active domain were joined together.

The plasmid carrying the artificial transcription factor gene was used as a template in PCR to amplify a gene fragment for koji mold transformation using primers 19 and 20 using DNA polymerase (manufactured by Toyobo Co., Ltd., product name: KOD-plus-neo). The amplification product was purified using the purification kit to obtain the gene fragment for koji mold transformation.

Next, an *Aspergillus oryzae* HO2 strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NITE BP-01750) was transformed with the gene fragment for koji mold transformation according to the standard method of the PEG-calcium technique. Subsequently, the obtained transformants were screened for a strain capable of growing in a CD plate medium to obtain a transcription factor-producing strain.

Next, the transcription factor-producing strain was inoculated at $1 \times 10^6$ cells/plate to a CD medium supplemented with fluoroorotic acid monohydrate (manufactured by Wako Pure Chemical Industries, Ltd.) (final concentration: 1 mg/mL) and uridine (manufactured by Sigma-Aldrich Inc.) (final concentration: 20 mM) and screened for a strain capable of growing therein to obtain a uridine-auxotrophic transcription factor-producing strain.

The base sequences of the primers 1 to 20 are shown in Table 1.

TABLE 1

| Primer No. | Base sequence 5'→3' | SEQ ID NO | Remarks |
|---|---|---|---|
| 1 | ccggctcgtatgttgctggaccaaccgccaaggttag | 3 | Upstream sequence of tppA gene |
| 2 | actgaattgcaattaatggcggacaatg | 4 | Upstream sequence of tppA gene |
| 3 | tgtctcggaccttacgtgtcttagatgcgactcaatacaactgttc | 5 | Downstream sequence of tppA gene |
| 4 | tgggtaacgccagggttgaggctgaagacttaaatacgacattgc | 6 | Downstream sequence of tppA gene |
| 5 | ctgttacgcttccccgggtttgaaggtggtgcgaactttgtagttc | 7 | tef1 promoter gene |
| 6 | gtaaggtccgagacagtaagggattgatc | 8 | tef1 promoter gene |
| 7 | taattgcaattcagtagtaacccattcccggttctctagctg | 9 | agdA terminator gene |
| 8 | gtaacgccagggcccggggaagcgtaacaggatagcctagacccac | 10 | agdA terminator gene |
| 9 | ctgcaggatgattagcgtgcaaaccaagcaaacaagcatc | 11 | Gene fragment for marker recycling |
| 10 | actgaattgcaattaatggcggacaatg | 12 | Gene fragment for marker recycling |
| 11 | taattgcaattcagtgcaagctcgagcatccaactaaactag | 13 | Gene cassette for prG gene expression |

TABLE 1-continued

| Primer No. | Base sequence 5'→3' | SEQ ID NO | Remarks |
|---|---|---|---|
| 12 | tgggtaacgccagggcccgggctaatcatcctgcagctccgtcattg | 14 | Gene cassette for prG gene expression |
| 13 | ccctggcgttacccaacttaatcg | 15 | Plasmid-derived gene fragment |
| 14 | caacatacgagccggaagcataaagtg | 16 | Plasmid-derived gene fragment |
| 15 | cgcaccaccttcaaaatgtcgttgaataccgacgattccggtc | 17 | DBD of transcription factor kojR |
| 16 | acctaggttccagctaaacccgtacac | 18 | DBD of transcription factor kojR |
| 17 | atcctgttacgcttctcaaaacgaaatctcctccccagcc | 19 | AD of transcription factor AmyR |
| 18 | agctggaacctaggtgcactccccgcgccac | 20 | AD of transcription factor AmyR |
| 19 | cagtgagcgcaacgcaattaatgtgagttag | 21 | Gene fragment for koji mold transformation |
| 20 | gggatgtgctgcaaggcgattaagttg | 22 | Gene fragment for koji mold transformation |

[Construction of GUS-producing Strain with Cis Elements Linked]

First, a first gene fragment in which: 4 cis elements of SEQ ID NO: 1 were linked in tandem; restriction enzyme sites SphI and BamHI were added on the 5'-terminal side thereof; and BglII and NcoI sites were added on the 3'-terminal side thereof was prepared by oligo synthesis.

Next, the first gene fragment and a plasmid pPEA2 containing an *Aspergillus oryzae*-derived enoA promoter were each fragmented by treatment with restriction enzymes SphI and NcoI. These fragments were subjected to ligation reaction, and *E. coli* was then transformed with the ligation product to construct a plasmid pEA4K.

Next, the gene fragment was treated with a restriction enzyme BamHI, while the plasmid pEA4K was treated with restriction enzymes BglII and NcoI. These two treatment products were subjected to ligation reaction, and *E. coli* was then transformed with the ligation product to construct a plasmid pEA8K.

Next, the plasmid pEA8K was used as a template in PCR amplification using primers 21 and 22 and DNA polymerase (manufactured by Toyobo Co., Ltd., product name: KOD-plus-). The amplification product was purified using a purification kit (manufactured by Promega Corp., product name: Wizard SV Gel and PCR Clean-Up System) to obtain a second gene fragment.

Next, the genomic DNA of *Aspergillus oryzae* was used as a template in PCR amplification using primers 23 and 24 and DNA polymerase (manufactured by Toyobo Co., Ltd., product name: KOD-plus-). The amplification product was purified using a purification kit (manufactured by Promega Corp., product name: Wizard SV Gel and PCR Clean-Up System) to obtain a third gene fragment.

Next, the second gene fragment and the third gene fragment were used as a template in fusion PCR using primers 22 and 24 to prepare a fourth gene fragment in which the second gene fragment and the third gene fragment were joined together.

Next, a restriction enzyme-treated plasmid pPPG introduced with an *E. coli*-derived plasmid pMD20 (manufactured by Takara Bio Inc.) carrying upstream 1000 bp of *Aspergillus oryzae*-derived pyrG gene, an *Aspergillus oryzae*-derived pyrG expression cassette, and an *E. coli*-derived uidA gene was subjected to ligation reaction with a gene fragment for marker recycling obtained by PCR-amplifying a plasmid pPPG as a template using primers 25 and 26 and DNA polymerase (manufactured by Toyobo Co., Ltd., product name: KOD-plus-) and purifying the amplification product using a purification kit (manufactured by Promega Corp., product name: Wizard SV Gel and PCR Clean-Up System). Then, *E. coli* was transformed with the ligation product to construct a plasmid pPPRG.

Next, the plasmid pPPRG was used as a template in PCR amplification using primers 27 and 28 and DNA polymerase (manufactured by Toyobo Co., Ltd., product name: KOD-plus-). The amplification product was purified using a purification kit (manufactured by Promega Corp., product name: Wizard SV Gel and PCR Clean-Up System) to obtain a fifth gene fragment.

The fourth gene fragment and the fifth gene fragment were used as a template in fusion PCR using primers 24 and 27 to prepare a cis element-linked GUS (β-glucuronidase) production cassette gene fragment in which the fourth gene fragment and the fifth gene fragment were joined together.

Next, the uridine-auxotrophic transcription factor-producing strain was transformed using the cis element-linked GUS production cassette gene fragment according to the standard method of the PEG-calcium technique. Subsequently, the obtained transformants were screened for a strain capable of growing in a CD plate medium to obtain a GUS-producing strain with 8 cis elements linked in tandem.

The base sequences of the primers 21 to 28 are shown in Table 2.

TABLE 2

| Primer No. | Base sequence 5'→3' | SEQ ID NO |
|---|---|---|
| 21 | ccgctgctaggcgcgccgtgcactatagggcgaattgggc | 23 |
| 22 | tggggtttctacaggacgtaacattttgacgagctgcggaatt | 24 |
| 23 | cacggcgcgcctagcagcgggtagtggtggatacgtactcctt | 25 |
| 24 | ttcaggtcacgttctaagcttatcag | 26 |
| 25 | cccccctccggatgatgtagaagttgctcggtagctg | 27 |
| 26 | cccccctccggacaattgccgcgaaaaattaaattg | 28 |
| 27 | ccagaggtgactttatccaagatt | 29 |
| 28 | caattccgcagctcgtcaaaatgttacgtcctgtagaaacccca | 30 |

[GUS Activity Measurement Method]

The GUS-producing strain with 8 cis elements linked in tandem was cultured in a CD plate medium for 1 week to form spores. The spores were recovered using 0.01% POLYSORBATE 20 (manufactured by Wako Pure Chemical Industries, Ltd.) to obtain a spore suspension.

Next, 50 mL of a PD medium (2 mass/volume % of dextrin, 1 mass/volume % of polypeptone, 0.1 mass/volume % of casamino acid, 0.5 mass/volume % of potassium dihydrogen phosphate, 0.05 mass/volume % of magnesium sulfate, and 0.1 mass/volume % of sodium nitrate) was placed in a 200 mL Erlenmeyer flask, to which the spores were then inoculated at a final spore concentration of $1 \times 10^5$/mL.

Next, liquid culture was performed at 30° C. for 60 hours. After the completion of the culture, the bacterial cells were disrupted, and the disrupted powder was suspended in a buffer for intracellular protein extraction having the composition given below to obtain an extract.

[Composition of Buffer for Intracellular Protein Extraction]
$NaH_2PO_4.2H_2O$ (MW=156.01) (pH 7) 1.56 g (50 mM)
0.5 M EDTA 4 mL (10 mM)
Nonionic surfactant (manufactured by Sigma-Aldrich Inc., product name: Triton X-100) 0.2 g (0.1%)
N-Laurylsarcosinate Na 0.2 g (0.1%)
β-mercaptoethanol (MW=78.13) 142 μL (10 mM)
Distilled water 200 mL Next, the extract was added to a buffer for GUS activity measurement having the composition given below and reacted at 37° C. for 15 minutes. Then, the absorbance was measured at a wavelength of 415 nm to calculate an activity value (U). 1 U means the amount of the enzyme necessary for forming 1 mM PNP from PNP-Glucuronide (purine nucleoside phosphorylase-glucuronic acid inclusion) at 37° C. for 1 minute.

[Composition of Buffer for GUS Activity Measurement]
$NaH_2PO_4.2H_2O$ (MW=156.01) (pH 7) 1.56 g (50 mM)
β-mercaptoethanol (MW=78.13) 142 μL (10 mM)
Nonionic surfactant (manufactured by Sigma-Aldrich Inc., product name: Triton X-100) 0.2 g (0.1%)
p-Nitrophenyl β-D-glucuronic acid inclusion (MW=315.23) 63 mg (1 mM)
Distilled water 200 mL Next, the amount of the protein contained in the extract was measured using protein assay CBB solution (manufactured by Nacalai Tesque, Inc.), and the activity value was divided by the amount of the protein to calculate GUS activity (U/mg). The results are shown as a relative value of GUS activity in FIG. 4.

Figure 5:
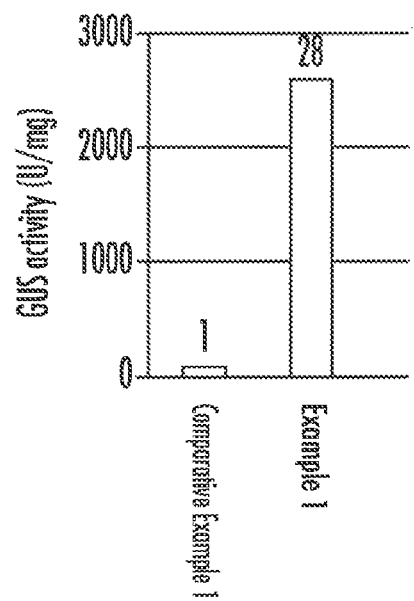
FIG. 5 is a graph showing GUS activity when the transformant of the present invention was cultured for 90 hours with dextrin as the substrate.

Also, GUS activity (U/mg) when the liquid culture was performed at 30° C. for 90 hours is shown in FIG. 5.

COMPARATIVE EXAMPLE 1

In this Comparative Example, a GUS-producing strain was constructed in totally the same way as in Example 1 except that the artificial transcription factor gene was not introduced and no cis element was linked.

Next, GUS activity was measured in totally the same way as in Example 1 except that the GUS-producing strain obtained in this Comparative Example was used.

A relative value of GUS activity (U/mg) when the liquid culture was performed at 30° C. for 60 hours is shown in FIG. 4. GUS activity (U/mg) when the liquid culture was performed at 30° C. for 90 hours is shown in FIG. 5.

From FIG. 4, when the GUS activity (U/mg) in which the liquid culture was performed at 30° C. for 60 hours with dextrin as a substrate is defined as 1 for the GUS-producing strain of Comparative Example 1 in which the artificial transcription factor gene was not introduced and no cis element was linked, it is obvious that 25.1 times GUS activity can be obtained in the GUS-producing strain of Example 1.

From FIG. 5, when the GUS activity (U/mg) when the liquid culture was performed at 30° C. for 90 hours with dextrin as a substrate is defined as 1 for the GUS-producing strain of Comparative Example 1 in which the artificial transcription factor gene was not introduced and no cis element was linked, it is obvious that 28 times GUS activity can be obtained in the GUS-producing strain of Example 1.

EXAMPLE 2

In this Example, GUS activity (U/mg) was calculated in totally the same way as in Example 1 except that 50 mL of a PG medium (2 mass/volume % of glucose, 1 mass/volume % of polypeptone, 0.1 mass/volume % of casamino acid, 0.5 mass/volume % of potassium dihydrogen phosphate, 0.05 mass/volume % of magnesium sulfate, and 0.1 mass/volume % of sodium nitrate) was placed in a 200 mL Erlenmeyer flask, to which the spores of the GUS-producing strain harboring 8 cis elements linked in tandem obtained in Example 1 were then inoculated at a final spore concentration of 1×10⁵/mL, followed by liquid culture at 30° C. for 60 hours. The results are shown in FIG. 6.

COMPARATIVE EXAMPLE 2

In this Comparative Example, GUS activity was measured in totally the same way as in Example 2 except that the GUS-producing strain obtained in Comparative Example 1 was used. GUS activity (U/mg) when the liquid culture was performed at 30° C. for 60 hours is shown in FIG. 6.

Figure 6:
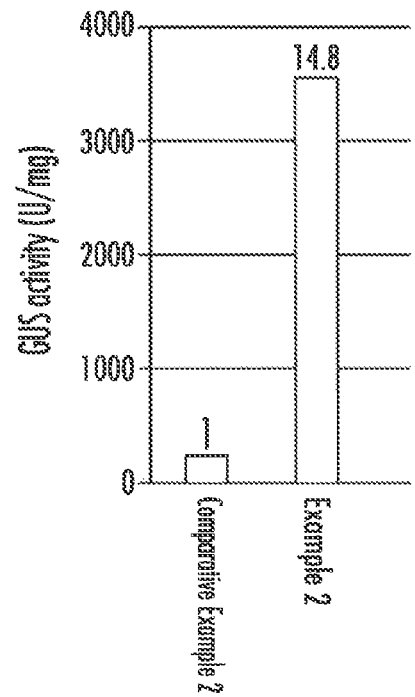
FIG. 6 is a graph showing GUS activity when the transformant of the present invention was cultured for 60 hours with glucose as a substrate.

From FIG. 6, when the GUS activity (U/mg) in which the liquid culture was performed at 30° C. for 60 hours with glucose as a substrate is defined as 1 for the GUS-producing strain of Comparative Example 2 in which the artificial transcription factor gene was not introduced and no cis element was linked, it is obvious that 14.8 times GUS activity can be obtained in the GUS-producing strain of Example 2.

EXAMPLE 3

(Construction of Transformant Introduced with Artificial Transcription Factor Gene (2))

In this Example, first, the genomic DNA gene of an *Aspergillus oryzae* HO4 strain (National Institute of Technology and Evaluation, Patent Microorganisms Depositary, #122, 2-5-8 Kazusakamatari, Kisarazu-shi, Chiba, Japan, Deposition Date: Dec. 9, 2014, Deposition No.: NITE BP-01980) was used as a template in PCR to amplify an upstream sequence of ligD gene using primers 29 and 30, its downstream sequence using primers 31 and 32, a marker recycling sequence using primers 33 and 34, and a pyrG gene using primers 35 and 36. DNA polymerase (manufactured by Toyobo Co., Ltd., product name: KOD FX neo) was used in each PCR amplification. The amplification products were each purified using a purification kit (manufactured by Qiagen N.V., product name: QIAquick PCR purification kit) to obtain a total of 4 gene fragments.

Next, an *E. coli*-derived plasmid pMD20 (manufactured by Takara Bio Inc.) was used as a template to obtain a gene fragment derived from the plasmid using primers 13 and 14.

Next, gene fragment of upstream sequence of ligD gene, gene fragment of its downstream sequence, and gene fragment of plasmid pMD20 were treated with a cloning kit (manufactured by Takara Bio Inc., product name: In-Fusion HD Cloning kit) and used in the transformation of an *E. coli* HST08 strain (manufactured by Takara Bio Inc.) to construct a plasmid pM-Ao Δ ligD.

Next, the plasmid pM-Ao Δ ligD was treated with the restriction enzyme SmaI (manufactured by Takara Bio Inc.) at 30° C. and purified using the purification kit to obtain the restriction treatment product of the plasmid pM-Ao Δ ligD (gene fragment).

Next, gene fragment of plasmid pM-Ao Δ ligD and gene fragment of pyrG gene were treated with the cloning kit and used in the transformation of an *E. coli* HST08 strain (manufactured by Takara Bio Inc.) to construct a plasmid pM-Ao Δ ligD::pyrG in which pyrG gene was introduced between the upstream sequence of ligD gene and its downstream sequence.

Next, the plasmid pM-Ao Δ ligD::pyrG was treated with the restriction enzyme SmaI (manufactured by Takara Bio Inc.) at 30° C. and purified using the purification kit to obtain the restriction treatment product of the plasmid pM-Ao Δ ligD::pyrG (gene fragment).

Next, gene fragment of plasmid pM-Ao Δ ligD::pyrG and gene fragment of the marker recycling sequence were treated with the cloning kit and used in the transformation of an *E. coli* HST08 strain (manufactured by Takara Bio Inc.) to construct a plasmid pM-Ao Δ ligD::pyrGR in which the marker recycling sequence was introduced between the downstream sequence of ligD gene and the pyrG gene.

Next, the plasmid pM-Ao Δ ligD::pyrGR was treated with the restriction enzyme SmaI (manufactured by Takara Bio Inc.) at 30° C. and purified using the purification kit to obtain the restriction treatment product of the plasmid pM-Ao Δ ligD::pyrGR (gene fragment).

Next, the genomic DNA gene of an *Aspergillus oryzae* HO4 strain (National Institute of Technology and Evaluation, Patent Microorganisms Depositary, #122, 2-5-8 Kazusakamatari, Kisarazu-shi, Chiba, Japan, Deposition Date: Dec. 9, 2014, Deposition No.: NITE BP-01980) was used as a template in PCR to amplify an enoA promoter gene using primers 37 and 38, and a plasmid introduced with the artificial transcription factor gene in which the DNA binding domain and the active domain were joined together prepared in Example 1 was used as a template in PCR to amplify an agdA terminator gene and an artificial transcription gene using primers 39 and 40. The DNA polymerase was used in each PCR amplification. The amplification products were each purified using the purification kit to obtain the DNA binding domain and the active domain.

Next, gene fragment of plasmid pM-Ao Δ ligD::pyrGR, gene fragment of enoA promoter gene, agdA terminator gene, and artificial transcription gene were treated with the cloning kit and used in the transformation of an *E. coli* HST08 strain (manufactured by Takara Bio Inc.) to construct a plasmid pM-Ao Δ ligD::pyrGR-TF1 in which artificial transcription factor gene was introduced between the upstream sequence of ligD gene and its downstream sequence.

The plasmidpM-Ao Δ ligD::pyrGR-TF1 carrying the artificial transcription factor gene was used as a template in PCR to amplify a gene fragment for koji mold transformation using primers 19 and 20 using the DNA polymerase. The amplification product was purified using the purification kit to obtain the gene fragment for koji mold transformation.

Next, an *Aspergillus oryzae* HO4 strain (National Institute of Technology and Evaluation, Patent Microorganisms Depositary, #122, 2-5-8 Kazusakamatari, Kisarazu-shi, Chiba, Japan, Deposition Date: Dec. 9, 2014, Deposition No.: NITE BP-01980) was transformed with the gene fragment for koji mold transformation according to the standard method of the PEG-calcium technique. Subsequently, the obtained transformants were screened for a strain capable of growing in a CD plate medium to obtain a transcription factor-producing strain.

Next, the transcription factor-producing strain was inoculated at 1×10⁶ cells/plate to a CD medium supplemented with fluoroorotic acid monohydrate (manufactured by Wako Pure Chemical Industries, Ltd.) (final concentration: 1 mg/mL) and uridine (manufactured by Sigma-Aldrich Inc.) (final concentration: 20 mM) and screened for a strain capable of growing therein to obtain a uridine-auxotrophic transcription factor-producing strain.

The base sequences of the primers 29 to 40 are shown in Table 3.

TABLE 3

| Primer No. | Base sequence 5'→3' | SEQ ID NO | Remarks |
|---|---|---|---|
| 29 | tcgagctcgg tacccggtta ctgctctccc ttgatgatg | 31 | Upstream sequence of ligD gene |
| 30 | taggtagtga acctatttcg agagcag | 32 | Upstream sequence of ligD gene |
| 31 | taggttcact acctagcggc cgcacaggca ccttgcatca tcatc | 33 | Downstream sequence of ligD gene |
| 32 | ctctagagga tccccggacc gacgattcgt tgaagag | 34 | Downstream sequence of ligD gene |
| 33 | aggtatcgaa ttcccgacga gctcgtacag atctttg | 35 | marker recycling sequence |
| 34 | ccatgggaaa tgcccgggag agcagagtgc atggaatact ag | 36 | marker recycling sequence |
| 35 | gcactctgct ctcccggtgg tgggaaatct tgtatataat tgtgattg | 37 | pyG gene |
| 36 | ccatgggaaa tgcccgggcg acactggaag aactgcttga agag | 38 | pyG gene |
| 37 | cctgccgcga gatctgggca tttcccatgg gcctaaccca aatc | 39 | enoA promoter gene |
| 38 | ccatgggaaa tgcccagatc tcgcggcagg gttgacacag ttgac | 40 | enoA promoter gene |
| 39 | gcactctgct ctcccagtaa cccattcccg gttctctagc | 41 | *1 |
| 40 | atgtcgttga ataccgacga ttccggtc | 42 | *1 |

*1: agdA terminator gene, artificial transcription gene

[Construction of CBH1 Producing Strain with Cis Elements Linked]

First, the genomic DNA gene of an *Aspergillus oryzae* HO4 strain (National Institute of Technology and Evaluation, Patent Microorganisms Depositary, #122, 2-5-8 Kazusakamatari, Kisarazu-shi, Chiba, Japan, Deposition Date: Dec. 9, 2014, Deposition No.: NITE BP-01980) was used as a template in PCR to amplify an upstream sequence of pyrG gene using primers 41 and 42, its downstream sequence using primers 43 and 44. A cis element-linked GUS (β-glucuronidase) production cassette gene fragment obtained in Example 1 was used as a template in PCR to amplify a cis element linked promoter gene using primers 45 and 46, agdA terminator gene using primers 47 and 48. The genomic DNA gene of an *Acremonium cellulolyticus* H1 strain (National Institute of Technology and Evaluation, Patent Microorganisms Depositary, #122, 2-5-8 Kazusakamatari, Kisarazu-shi, Chiba, Japan, Deposition Date: Sep. 5, 2011, Deposition No.: FERM BP-11508) was used as a template in PCR to amplify a cellobiohydrolase (cbh1) gene using primers 49 and 50. The genomic DNA gene of an *Aspergillus awamori* HA1 strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NITE BP-01751) was used as a template in PCR to amplify a gene cassette for pyrG gene expression using primers 51 and 52. DNA polymerase was used in each PCR amplification. The amplification products were each purified using the purification kit to obtain a total of 6 gene fragments.

Next, plasmid pMD20 (manufactured by Takara Bio Inc.) was treated with a restriction enzyme SmaI (manufactured by Takara Bio Inc.) at 30° C. and purified using the purification kit to obtain the restriction treatment product of the plasmid pMD20 (gene fragment).

Next, gene fragment of the upstream sequence of pyrG gene, gene fragment of its downstream sequence, gene fragment of the cis element linked promoter gene, gene fragment of the agdA terminator gene, gene fragment of the bch1 gene, gene fragment of the gene cassette for pyrG gene expression, and gene fragment of the plasmid pMD20 were sequentially treated with the cloning kit and used in the transformation of an *E. coli* HST08 strain (manufactured by Takara Bio Inc.) to construct a plasmid pPPeA8-CBH1.

Next, the plasmid pPPeA8-CBH1 was used as a template in PCR amplification using primers 19 and 20 and using DNA polymerase. The amplification product was purified using the purification kit to obtain a gene fragment for koji mold transformation (pyrG-CBH1 fragment).

Next, the *Aspergillus oryzae* HO4 strain (National Institute of Technology and Evaluation, Patent Microorganisms Depositary, #122, 2-5-8 Kazusakamatari, Kisarazu-shi, Chiba, Japan, Deposition Date: Dec. 9, 2014, Deposition No.: NITE BP-01980) was transformed using the gene fragment for koji mold transformation (pyrG-CBH1 fragment) according to the standard method of the PEG-calcium technique. Subsequently, the obtained transformants were screened for a strain capable of growing in a CD plate medium to obtain a transformant which corresponds to the transformant of Example 1.

The transformant is introduced with cellobiohydrolase (cbh1) gene in the chromosome, and is capable of producing cellobiohydrolase. Hereinafter, a transformant introduced with cbh1 gene in the chromosome and capable of producing cellobiohydrolase is abbreviated as "CBH1 producing strain".

The base sequences of the primers 41 to 52 are shown in Table 4.

TABLE 4

| Primer No. | Base sequence 5'→3' | SEQ ID NO | Remarks |
|---|---|---|---|
| 41 | ggatatcgga tcccccaga ggtgacttta tccaagattc cttc | 43 | Upstream sequence of pyrG gene |
| 42 | caattgccgc gaaaaattaa attgaatcta tg | 44 | Upstream sequence of pyrG gene |
| 43 | gtagtggtggatacgtactccttttatg | 45 | Downstream sequence of pyrG gene |
| 44 | tcgagctcgg taccctccag gtcacgttct aagcttatca gctg | 46 | Downstream sequence of pyrG gene |
| 45 | cgtatccaccactaccactatagggcgaattgggcccgac | 47 | PeA8 promotor gene |
| 46 | gttcaaggcagacattttgacgagctgcggaattggtcag | 48 | PeA8 promotor gene |
| 47 | ccaccactac cccgggaagc gtaacaggat agcctagacc | 49 | agdA terminator gene |
| 48 | ctgcaggatg attagagtaa cccattcccg gttctctagc tg | 50 | agdA terminator gene |
| 49 | atgtctgcct tgaactcttt caatatgtac aag | 51 | cbh1 gene |
| 50 | atcctgttac gcttcctaca aacattgaga gtagtaaggg ttcacg | 52 | cbh1 gene |
| 51 | ctaatcatcctgcagctccgtcattg | 53 | Cassette for pyrG gene expression |
| 52 | ttttcgcggcaattggcaagctcgagcatccaactaaactag | 54 | Cassette for pyrG gene expression |

[Enzyme Production Amount Measurement Method]

In order to measure the enzyme (cellobiohydrolase) production amount by the CBH1 producing strain, first, the CBH1 producing strain with 8 cis elements linked in tandem was cultured in a CD plate medium for 1 week to form spores. The spores were recovered using 0.01% POLYSORBATE 20 (manufactured by Wako Pure Chemical Industries, Ltd.) to obtain a spore suspension.

Next, 30 mL of a PD medium (2 mass/volume % of dextrin, 1 mass/volume % of polypeptone, 0.1 mass/volume % of casamino acid, 0.5 mass/volume % of potassium dihydrogen phosphate, 0.05 mass/volume % of magnesium sulfate, and 0.1 mass/volume % of sodium nitrate) was placed in a 100 mL Erlenmeyer flask, to which the spores were inoculated at a final spore concentration of $1\times10^4$/mL.

Next, liquid culture was performed at 30° C. for 6 days, to obtain a culture solution of CBH1 producing strain in which cellobiohydrolase (CBH1) was secreted and expressed in the culture medium.

Figure 7:
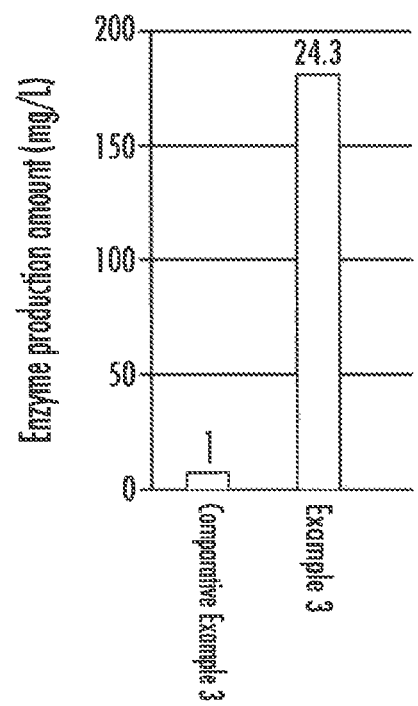
FIG. 7 is a graph showing CBH1 production amount when the transformant of the present invention was cultured for 6 days with dextrin as a substrate

Next, the CBH1 concentration in the culture solution was measured by SDS-PAGE analysis. BSA of 0.25 μg, 0.5 μg, and 2 μg were migrated at the same time as the reference of the protein, and the CBH1 concentration in the culture solution 10 μL was calculated by image analysis using an image automatic detection system (manufactured by BIO-RAD Corporation, product name: ChemiDoc XRS+system). The result is shown in FIG. 7.

COMPARATIVE EXAMPLE 3

In this Comparative Example, a CBH1 producing strain was constructed in totally the same way as in Example 3 except that the artificial transcription factor gene was not introduced and no cis element was linked.

Next, the CBH1 concentration in the culture solution was measured in totally the same way as in Example 3 except that the CBH1 producing strain obtained in this Comparative Example was used. The result is shown in FIG. 7.

From FIG. 7, when the liquid culture was performed at 30° C. for 6 days with dextrin as a substrate, according to the CBH1 producing strain of Example 3, it is obvious that 24.3 times enzyme (cellobiohydrolase, CBH1) can be produced compared to the CBH1 producing strain of Comparative Example 3 in which the artificial transcription factor gene was not introduced and no cis element was linked.

REFERENCE SIGNS LIST 1 base sequence for protein expression
2 protein
3 gene
4 promoter
5 cis element
6 artificial transcription factor Sequence Listing

```
<110>    HONDA MOTOR CO., LTD.
<120>    Base sequence for protein expression and production of protein
<130>    PCT160077
<160>    30
<170>    PatentIn version 3.5
```

Sequence Listing

```
<210>   1
<211>   20
<212>   DNA
<213>   Aspergillus oryzae

<400>   1
gacggaaaag tcgggtagat                                              20

<210>   2
<211>   1872
<212>   DNA
<213>   Aspergillus oryzae

<400>   2 atgtcgttga ataccgacga ttccggtcgg ataaggaccc ggcaacgcgc caaaagagcg    60
tgcgaaacgt gcaaactgcg caagaggaaa tgtgacggcc atgagccctg cacttactgc   120
ttgcgatacg aatatcagtg cactttcaag cctcatccac ggagaaagcc tgcagcttcc   180
aaatcttccg cacggcccag cgaggaagaa gactcaccaa agtttctcga cagagttgat   240
gctaaccaag aacacatgga ggccaactca ggcaccgctt tccccatct cctagggatg    300 aggttgaacc cgcagggtgc tcccaaggtg tacgggttta gctggaacct aggtgcactc   360
cccgcgccac gccgtctgtc gacgccaaac cttctagccc atgtcaatgt cttcctcaag   420
tacctgttcc cgatcatgcc cgtcgtgaga caggaccagc tgcagcagga ctgccaccag   480
ccggagcgct tgtctcccca cgctacgct ttcattgccg ctctatgcgc ggccacgcac    540
atccaactga agctggacgg tgcagcaccg ggtcccgagg cggcttccgc gcgagccagc   600
ctcgacggac atcctatgtt gtcgggagaa gaactcctgg ctgaagccgt gcgcgcaaga   660
aaggaataca acgtggtcga cgaaattaac atggaaaacc tcctaacctc cttctttctc   720
ttcgccgcct acggaaacct agacagacag gatcaggcct ggttctacct atgtcagacc   780
acgtccatgg tcttcacact aggcctacaa cgggaatcca catactcgaa actaagcgtc   840
gaggaagcag aagagaaaag gagagtattc tggctcttat tcgtcacaga aaggtaagaa   900
aagaaaaaac tctactttcc caatcaccac cacgtaccaa aaataacacg aaaaaccaga   960
ggctacgcat tacaacaagc aaaaccagtc atgctccgca actccatcca caaaccacag  1020
gtcctgtgct cagacgaccc aatcctagcc tacggcttca tcaacctcat caacgtcttc  1080
gaaaagctca gcccaaatct ctacgactgg gtctccgccg gcggcagcag cgcagacggc  1140 gacccccgc ctacttcttc tatccaatcc agtctcgcca agcaaatctc cctcgagggc   1200
gtctccgaga tccagaaagt agacatcctc atcactcagc aatggctaca aaccatgatg  1260
tggaaactct ccatgaccca cgtcacacag cccggctctc gcgatgacgc cgttctcccc  1320
ttccacctgc ccgtgctagt cggcaaggcc gtcatgggcg tcatcgccgc ggcatcccaa  1380
ggtgctgttg acgctcatgg tatcggaatg gtaagaaagc gaccttacct catcacaccc  1440
tccctcatca gtcactcccc atcatctata cccgcaatct aacaaaaacc gcaggaacaa  1500
aaactctacg acctcggcac ctccgtagcc gacgtctccc gctccctaag cacaaaagcc  1560
gcccaccacc tcgccgaatc gaccatcgac ccccgagaac tcctctgggg cattctcaca  1620
acctatcccc gaatccgcgg ttcccaatca tacctcttcc cagcgctcgt cgagcaaagt  1680
cgaggcatca tcagtttcga ctgttcgctt tccatcagtg actttctgcc ttcgtttggt  1740
gggccgccgg ctattatgtg gcggacgggt gaatctgggt ttgatttatt ggggatcgcg  1800
gatgatttgc aagagaggga gaatgagggt ggggagggga ttgtggtggc tggggaggag  1860
```

| Sequence Listing |
|---| atttcgatt ga                                                                   1872

<210>   3
<211>   37
<212>   DNA
<213>   *Aspergillus oryzae*

<400>   3 ccggctcgta tgttgctgga ccaaccgcca aggttag                                         37

<210>   4
<211>   28
<212>   DNA
<213>   *Aspergillus oryzae*

<400>   4 actgaattgc aattaatggc ggacaatg                                                   28

<210>   5
<211>   46
<212>   DNA
<213>   *Aspergillus oryzae*

<400>   5 tgtctcggac cttacgtgtc ttagatgcga ctcaatacaa ctgttc                               46

<210>   6
<211>   45
<212>   DNA
<213>   *Aspergillus oryzae*

<400>   6 tgggtaacgc cagggttgag gctgaagact taaatacgac attgc                                45

<210>   7
<211>   46
<212>   DNA
<213>   *Aspergillus oryzae*

<400>   7 ctgttacgct tccccgggtt tgaaggtggt gcgaactttg tagttc                               46

<210>   8
<211>   29
<212>   DNA
<213>   *Aspergillus oryzae*

<400>   8 gtaaggtccg agacagtaag ggattgatc                                                  29

<210>   9
<211>   42
<212>   DNA
<213>   *Aspergillus oryzae*

<400>   9 taattgcaat tcagtagtaa cccattcccg gttctctagc tg                                   42

<210>   10
<211>   46
<212>   DNA
<213>   *Aspergillus oryzae*

<400>   10 gtaacgccag ggcccgggga agcgtaacag gatagcctag acccac                               46

<210>   11
<211>   40
<212>   DNA
<213>   *Aspergillus oryzae*

<400>   11 ctgcaggatg attagcgtgc aaaccaagca acaagcatc                                       40

<210>   12
<211>   28
<212>   DNA

```
                              Sequence Listing
<213>   Aspergillus oryzae

<400>   12
actgaattgc aattaatggc ggacaatg                                          28

<210>   13
<211>   42
<212>   DNA
<213>   Aspergillus awamorii

<400>   13
taattgcaat tcagtgcaag ctcgagcatc caactaaact ag                          42

<210>   14
<211>   47
<212>   DNA
<213>   Aspergillus awamorii

<400>   14
tgggtaacgc cagggcccgg gctaatcatc ctgcagctcc gtcattg                     47

<210>   15
<211>   24
<212>   DNA
<213>   Escherichia coli

<400>   15
ccctggcgtt acccaactta atcg                                              24

<210>   16
<211>   27
<212>   DNA
<213>   Escherichia coli

<400>   16
caacatacga gccggaagca taaagtg                                           27

<210>   17
<211>   43
<212>   DNA
<213>   Aspergillus oryzae

<400>   17
cgcaccacct tcaaaatgtc gttgaatacc gacgattccg gtc                         43

<210>   18
<211>   27
<212>   DNA
<213>   Aspergillus oryzae

<400>   18
acctaggttc cagctaaacc cgtacac                                           27

<210>   19
<211>   40
<212>   DNA
<213>   Aspergillus oryzae

<400>   19
atcctgttac gcttctcaaa acgaaatctc ctccccagcc                             40

<210>   20
<211>   31
<212>   DNA
<213>   Aspergillus oryzae

<400>   20
agctggaacc taggtgcact ccccgcgcca c                                      31

<210>   21
<211>   31
<212>   DNA
<213>   Aspergillus oryzae

<400>   21
cagtgagcgc aacgcaatta atgtgagtta g                                      31
```

| Sequence Listing |
|---|

```
<210>   22
<211>   27
<212>   DNA
<213>   Aspergillus oryzae

<400>   22
gggatgtgct gcaaggcgat taagttg                                          27

<210>   23
<211>   40
<212>   DNA
<213>   Aspergillus oryzae

<400>   23
ccgctgctag gcgcgccgtg cactatagggg cgaattgggc                           40

<210>   24
<211>   44
<212>   DNA
<213>   Aspergillus oryzae

<400>   24
tggggtact acaggacgta acattttgac gagctgcgga attg                        44

<210>   25
<211>   43
<212>   DNA
<213>   Aspergillus oryzae

<400>   25
cacggcgcgc ctagcagcgg gtagtggtgg atacgtactc ctt                        43

<210>   26
<211>   26
<212>   DNA
<213>   Aspergillus oryzae

<400>   26
ttcaggtcac gttctaagct tatcag                                           26

<210>   27
<211>   37
<212>   DNA
<213>   Aspergillus oryzae

<400>   27
ccccctccg gatgatgtag aagttgctcg gtagctg                                37

<210>   28
<211>   36
<212>   DNA
<213>   Aspergillus oryzae

<400>   28
ccccctccg gacaattgcc gcgaaaaatt aaattg                                 36

<210>   29
<211>   24
<212>   DNA
<213>   Aspergillus oryzae

<400>   29
ccagaggtga ctttatccaa gatt                                             24

<210>   30
<211>   44
<212>   DNA
<213>   Aspergillus oryzae

<400>   30
caattccgca gctcgtcaaa atgttacgtc ctgtagaaac ccca                       44

<210>   31
<211>   39
<212>   DNA
<213>   Aspergillus oryzae
```

Sequence Listing

```
<400>   31
tcgagctcgg tacccggtta ctgctctccc ttgatgatg              39

<210>   32
<211>   27
<212>   DNA
<213>   Aspergillus oryzae

<400>   32
taggtagtga acctatttcg agagcag                           27

<210>   33
<211>   45
<212>   DNA
<213>   Aspergillus oryzae

<400>   33
taggttcact acctagcggc cgcacaggca ccttgcatca tcatc       45

<210>   34
<211>   37
<212>   DNA
<213>   Aspergillus oryzae

<400>   34
ctctagagga tccccggacc gacgattcgt tgaagag                37

<210>   35
<211>   37
<212>   DNA
<213>   Aspergillus oryzae

<400>   35
aggtatcgaa ttcccgacga gctcgtacag atcatg                 37

<210>   36
<211>   42
<212>   DNA
<213>   Aspergillus oryzae

<400>   36
ccatgggaaa tgcccgggag agcagagtgc atggaatact ag          42

<210>   37
<211>   48
<212>   DNA
<213>   Aspergillus oryzae

<400>   37
gcactctgct ctcccggtgg tgggaaatct tgtatataat tgtgattg    48

<210>   38
<211>   44
<212>   DNA
<213>   Aspergillus oryzae

<400>   38
ccatgggaaa tgcccgggcg acactggaag aactgcttga agag        44

<210>   39
<211>   44
<212>   DNA
<213>   Aspergillus oryzae

<400>   39
cctgccgcga gatctgggca tacccatgg gcctaaccca aatc         44

<210>   40
<211>   45
<212>   DNA
<213>   Aspergillus oryzae

<400>   40
ccatgggaaa tgcccagatc tcgcggcagg gttgacacag ttgac       45

<210>   41
<211>   40
```

| Sequence Listing |
|---|

<212> DNA
<213> Aspergillus oryzae

<400> 41
gcactctgct ctcccagtaa cccattcccg gttctctagc                    40

<210> 42
<211> 44
<212> DNA
<213> Aspergillus oryzae

<400> 42
atgtcgttga ataccgacga ttccggtc                                 28

<210> 43
<211> 44
<212> DNA
<213> Aspergillus oryzae

<400> 43
ggatatcgga tccccccaga ggtgacttta tccaagattc cttc               44

<210> 44
<211> 32
<212> DNA
<213> Aspergillus oryzae

<400> 44
caattgccgc gaaaaattaa attgaatcta tg                            32

<210> 45
<211> 28
<212> DNA
<213> Aspergillus oryzae

<400> 45
gtagtggtgg atacgtactc cattatg                                  28

<210> 46
<211> 44
<212> DNA
<213> Aspergillus oryzae

<400> 46
tcgagctcgg taccctttcag gtcacgttct aagcttatca gctg              44

<210> 47
<211> 40
<212> DNA
<213> Aspergillus oryzae

<400> 47
cgtatccacc actaccacta tagggcgaat tgggcccgac                    40

<210> 48
<211> 40
<212> DNA
<213> Aspergillus oryzae

<400> 48
gttcaaggca gacanttga cgagctgcgg aattggtcag                     40

<210> 49
<211> 40
<212>
<213> Aspergillus oryzae

<400> 49
ccaccactac cccgggaagc gtaacaggat agcctagacc                    40

<210> 50
<211> 42
<212> DNA
<213> Aspergillus oryzae

<400> 50
ctgcaggatg attagagtaa cccattcccg gttctctagc tg                 42

Sequence Listing

```
<210>   51
<211>   33
<212>   DNA
<213>   Acremonium cellulolyticus

<400>   51
atgtctgcct tgaactcnt caatatgtac aag                              33

<210>   52
<211>   46
<212>
<213>   Acremonium cellulolyticus

<400>   52
atcctgttac gcttcctaca acattgaga gtagtaaggg ttcacg                 46

<210>   53
<211>   26
<212>   DNA
<213>   Aspergillus oryzae

<400>   53
ctaatcatcc tgcagctccg tcattg                                     26

<210>   54
<211>   42
<212>   DNA
<213>   Aspergillus oryzae

<400>   54
tatcgcggc aattggcaag ctcgagcatc caactaaact ag                    42
```

SEQUENCE LISTING

```
<160> NUMBER OF SEQ ID NOS: 54

<210> SEQ ID NO 1
<211> LENGTH: 20
<212> TYPE: DNA
<213> ORGANISM: Aspergillus oryzae

<400> SEQUENCE: 1
gacggaaaag tcgggtagat                                            20

<210> SEQ ID NO 2
<211> LENGTH: 1872
<212> TYPE: DNA
<213> ORGANISM: Aspergillus oryzae

<400> SEQUENCE: 2
atgtcgttga ataccgacga ttccggtcgg ataaggaccc ggcaacgcgc caaaagagcg    60
tgcgaaacgt gcaaactgcg caagaggaaa tgtgacggcc atgagccctg cacttactgc   120
ttgcgatacg aatatcagtg cactttcaag cctcatccac ggagaaagcc tgcagcttcc   180
aaatcttccg cacggcccag cgaggaagaa gactcaccaa gtttctcga cagagttgat    240 gctaaccaag aacacatgga ggccaactca ggcaccgctt cccccatct cctagggatg    300 aggttgaacc cgcagggtgc tcccaaggtg tacgggttta gctggaacct aggtgcactc   360
cccgcgccac gccgtctgtc gacgccaaac cttctagccc atgtcaatgt cttcctcaag   420
tacctgttcc cgatcatgcc cgtcgtgaga caggaccagc tgcagcagga ctgccaccag   480
ccggagcgct tgtctcccca acgctacgct tcattgccg ctctatgcgc ggccacgcac   540
atccaactga agctggacgg tgcagcaccg ggtcccgagg cggcttccgc gcgagccagc   600
```

-continued

```
ctcgacggac atcctatgtt gtcgggagaa gaactcctgg ctgaagccgt gcgcgcaaga    660
aaggaataca acgtggtcga cgaaattaac atggaaaacc tcctaacctc cttctttctc    720
ttcgccgcct acggaaacct agacagacag gatcaggcct ggttctacct atgtcagacc    780
acgtccatgg tcttcacact aggcctacaa cgggaatcca catactcgaa actaagcgtc    840
gaggaagcag aagagaaaag gagagtattc tggctcttat tcgtcacaga aggtaagaa     900 aagaaaaaac tctactttcc caatcaccac cacgtaccaa aaataacacg aaaaaccaga    960
ggctacgcat tacaacaagc aaaaccagtc atgctccgca actccatcca caaaccacag   1020
gtcctgtgct cagacgaccc aatcctagcc tacggcttca tcaacctcat caacgtcttc   1080
gaaaagctca gcccaaatct ctacgactgg gtctccgccg gcggcagcag cgcagacggc   1140
gaccccccgc ctacttcttc tatccaatcc agtctcgcca gcaaatctc cctcgagggc    1200 gtctccgaga tccagaaagt agacatcctc atcactcagc aatggctaca aaccatgatg   1260
tggaaactct ccatgaccca cgtcacacag cccggctctc gcgatgacgc cgttctcccc   1320
ttccacctgc ccgtgctagt cggcaaggcc gtcatgggcg tcatcgccgc ggcatcccaa   1380
ggtgctgttg acgctcatgg tatcggaatg gtaagaaagc gaccttacct catcacaccc   1440
tccctcatca gtcactcccc atcatctata cccgcaatct aacaaaaacc gcaggaacaa   1500
aaactctacg acctcggcac ctccgtagcc gacgtctccc gctccctaag cacaaaagcc   1560
gcccaccacc tcgccgaatc gaccatcgac ccccgagaac tcctctgggg cattctcaca   1620
accctatccc gaatccgcgg ttcccaatca tacctcttcc cagcgctcgt cgagcaaagt   1680
cgaggcatca tcagtttcga ctgttcgctt tccatcagtg actttctgcc ttcgtttggt   1740
gggccgccgg ctattatgtg gcggacgggt gaatctgggt ttgatttatt ggggatcgcg   1800
gatgatttgc aagagaggga gaatgagggt ggggagggga ttgtggtggc tggggaggag   1860
atttcgtttt ga                                                      1872
```

<210> SEQ ID NO 3
<211> LENGTH: 37
<212> TYPE: DNA
<213> ORGANISM: Aspergillus oryzae

<400> SEQUENCE: 3

```
ccggctcgta tgttgctgga ccaaccgcca aggttag                              37
```

<210> SEQ ID NO 4
<211> LENGTH: 28
<212> TYPE: DNA
<213> ORGANISM: Aspergillus oryzae

<400> SEQUENCE: 4

```
actgaattgc aattaatggc ggacaatg                                        28
```

<210> SEQ ID NO 5
<211> LENGTH: 46
<212> TYPE: DNA
<213> ORGANISM: Aspergillus oryzae

<400> SEQUENCE: 5

```
tgtctcggac cttacgtgtc ttagatgcga ctcaatacaa ctgttc                    46
```

<210> SEQ ID NO 6
<211> LENGTH: 45
<212> TYPE: DNA

<213> ORGANISM: Aspergillus oryzae

<400> SEQUENCE: 6
tgggtaacgc cagggttgag gctgaagact taaatacgac attgc    45

<210> SEQ ID NO 7
<211> LENGTH: 46
<212> TYPE: DNA
<213> ORGANISM: Aspergillus oryzae

<400> SEQUENCE: 7
ctgttacgct tccccgggtt tgaaggtggt gcgaactttg tagttc    46

<210> SEQ ID NO 8
<211> LENGTH: 29
<212> TYPE: DNA
<213> ORGANISM: Aspergillus oryzae

<400> SEQUENCE: 8
gtaaggtccg agacagtaag ggattgatc    29

<210> SEQ ID NO 9
<211> LENGTH: 42
<212> TYPE: DNA
<213> ORGANISM: Aspergillus oryzae

<400> SEQUENCE: 9
taattgcaat tcagtagtaa cccattcccg gttctctagc tg    42

<210> SEQ ID NO 10
<211> LENGTH: 46
<212> TYPE: DNA
<213> ORGANISM: Aspergillus oryzae

<400> SEQUENCE: 10
gtaacgccag ggcccgggga agcgtaacag gatagcctag acccac    46

<210> SEQ ID NO 11
<211> LENGTH: 40
<212> TYPE: DNA
<213> ORGANISM: Aspergillus oryzae

<400> SEQUENCE: 11
ctgcaggatg attagcgtgc aaaccaagca aacaagcatc    40

<210> SEQ ID NO 12
<211> LENGTH: 28
<212> TYPE: DNA
<213> ORGANISM: Aspergillus oryzae

<400> SEQUENCE: 12
actgaattgc aattaatggc ggacaatg    28

<210> SEQ ID NO 13
<211> LENGTH: 42
<212> TYPE: DNA
<213> ORGANISM: Aspergillus awamorii

<400> SEQUENCE: 13
taattgcaat tcagtgcaag ctcgagcatc caactaaact ag    42

<210> SEQ ID NO 14
<211> LENGTH: 47

<210> SEQ ID NO 14
<211> LENGTH: 47
<212> TYPE: DNA
<213> ORGANISM: Aspergillus awamorii

<400> SEQUENCE: 14
tgggtaacgc cagggcccgg gctaatcatc ctgcagctcc gtcattg            47

<210> SEQ ID NO 15
<211> LENGTH: 24
<212> TYPE: DNA
<213> ORGANISM: Escherichia coli

<400> SEQUENCE: 15
ccctggcgtt acccaactta atcg                                      24

<210> SEQ ID NO 16
<211> LENGTH: 27
<212> TYPE: DNA
<213> ORGANISM: Escherichia coli

<400> SEQUENCE: 16
caacatacga gccggaagca taaagtg                                   27

<210> SEQ ID NO 17
<211> LENGTH: 43
<212> TYPE: DNA
<213> ORGANISM: Aspergillus oryzae

<400> SEQUENCE: 17
cgcaccacct tcaaaatgtc gttgaatacc gacgattccg gtc                 43

<210> SEQ ID NO 18
<211> LENGTH: 27
<212> TYPE: DNA
<213> ORGANISM: Aspergillus oryzae

<400> SEQUENCE: 18
acctaggttc cagctaaacc cgtacac                                   27

<210> SEQ ID NO 19
<211> LENGTH: 40
<212> TYPE: DNA
<213> ORGANISM: Aspergillus oryzae

<400> SEQUENCE: 19
atcctgttac gcttctcaaa acgaaatctc ctccccagcc                     40

<210> SEQ ID NO 20
<211> LENGTH: 31
<212> TYPE: DNA
<213> ORGANISM: Aspergillus oryzae

<400> SEQUENCE: 20
agctggaacc taggtgcact ccccgcgcca c                              31

<210> SEQ ID NO 21
<211> LENGTH: 31
<212> TYPE: DNA
<213> ORGANISM: Aspergillus oryzae

<400> SEQUENCE: 21
cagtgagcgc aacgcaatta atgtgagtta g                              31

<210> SEQ ID NO 22

```
<211> LENGTH: 27
<212> TYPE: DNA
<213> ORGANISM: Aspergillus oryzae

<400> SEQUENCE: 22
gggatgtgct gcaaggcgat taagttg                                          27

<210> SEQ ID NO 23
<211> LENGTH: 40
<212> TYPE: DNA
<213> ORGANISM: Aspergillus oryzae

<400> SEQUENCE: 23
ccgctgctag gcgcgccgtg cactataggg cgaattgggc                            40

<210> SEQ ID NO 24
<211> LENGTH: 44
<212> TYPE: DNA
<213> ORGANISM: Aspergillus oryzae

<400> SEQUENCE: 24
tggggtttct acaggacgta acattttgac gagctgcgga attg                       44

<210> SEQ ID NO 25
<211> LENGTH: 43
<212> TYPE: DNA
<213> ORGANISM: Aspergillus oryzae

<400> SEQUENCE: 25
cacggcgcgc ctagcagcgg gtagtggtgg atacgtactc ctt                        43

<210> SEQ ID NO 26
<211> LENGTH: 26
<212> TYPE: DNA
<213> ORGANISM: Aspergillus oryzae

<400> SEQUENCE: 26
ttcaggtcac gttctaagct tatcag                                           26

<210> SEQ ID NO 27
<211> LENGTH: 37
<212> TYPE: DNA
<213> ORGANISM: Aspergillus oryzae

<400> SEQUENCE: 27
cccccctccg gatgatgtag aagttgctcg gtagctg                               37

<210> SEQ ID NO 28
<211> LENGTH: 36
<212> TYPE: DNA
<213> ORGANISM: Aspergillus oryzae

<400> SEQUENCE: 28
cccccctccg gacaattgcc gcgaaaaatt aaattg                                36

<210> SEQ ID NO 29
<211> LENGTH: 24
<212> TYPE: DNA
<213> ORGANISM: Aspergillus oryzae

<400> SEQUENCE: 29
ccagaggtga ctttatccaa gatt                                             24
```

<210> SEQ ID NO 30
<211> LENGTH: 44
<212> TYPE: DNA
<213> ORGANISM: Aspergillus oryzae

<400> SEQUENCE: 30
caattccgca gctcgtcaaa atgttacgtc ctgtagaaac ccca     44

<210> SEQ ID NO 31
<211> LENGTH: 39
<212> TYPE: DNA
<213> ORGANISM: Aspergillus oryzae

<400> SEQUENCE: 31
tcgagctcgg tacccggtta ctgctctccc ttgatgatg     39

<210> SEQ ID NO 32
<211> LENGTH: 27
<212> TYPE: DNA
<213> ORGANISM: Aspergillus oryzae

<400> SEQUENCE: 32
taggtagtga acctatttcg agagcag     27

<210> SEQ ID NO 33
<211> LENGTH: 45
<212> TYPE: DNA
<213> ORGANISM: Aspergillus oryzae

<400> SEQUENCE: 33
taggttcact acctagcggc cgcacaggca ccttgcatca tcatc     45

<210> SEQ ID NO 34
<211> LENGTH: 37
<212> TYPE: DNA
<213> ORGANISM: Aspergillus oryzae

<400> SEQUENCE: 34
ctctagagga tccccggacc gacgattcgt tgaagag     37

<210> SEQ ID NO 35
<211> LENGTH: 37
<212> TYPE: DNA
<213> ORGANISM: Aspergillus oryzae

<400> SEQUENCE: 35
aggtatcgaa ttcccgacga gctcgtacag atctttg     37

<210> SEQ ID NO 36
<211> LENGTH: 42
<212> TYPE: DNA
<213> ORGANISM: Aspergillus oryzae

<400> SEQUENCE: 36
ccatgggaaa tgcccgggag agcagagtgc atggaatact ag     42

<210> SEQ ID NO 37
<211> LENGTH: 48
<212> TYPE: DNA
<213> ORGANISM: Aspergillus oryzae

<400> SEQUENCE: 37
gcactctgct ctcccggtgg tgggaaatct tgtatataat tgtgattg     48

```
<210> SEQ ID NO 38
<211> LENGTH: 44
<212> TYPE: DNA
<213> ORGANISM: Aspergillus oryzae

<400> SEQUENCE: 38
ccatgggaaa tgcccgggcg acactggaag aactgcttga agag            44

<210> SEQ ID NO 39
<211> LENGTH: 44
<212> TYPE: DNA
<213> ORGANISM: Aspergillus oryzae

<400> SEQUENCE: 39
cctgccgcga gatctgggca tttcccatgg gcctaaccca aatc            44

<210> SEQ ID NO 40
<211> LENGTH: 45
<212> TYPE: DNA
<213> ORGANISM: Aspergillus oryzae

<400> SEQUENCE: 40
ccatgggaaa tgcccagatc tcgcggcagg gttgacacag ttgac           45

<210> SEQ ID NO 41
<211> LENGTH: 40
<212> TYPE: DNA
<213> ORGANISM: Aspergillus oryzae

<400> SEQUENCE: 41
gcactctgct ctcccagtaa cccattcccg gttctctagc                 40

<210> SEQ ID NO 42
<211> LENGTH: 28
<212> TYPE: DNA
<213> ORGANISM: Aspergillus oryzae

<400> SEQUENCE: 42
atgtcgttga ataccgacga ttccggtc                              28

<210> SEQ ID NO 43
<211> LENGTH: 44
<212> TYPE: DNA
<213> ORGANISM: Aspergillus oryzae

<400> SEQUENCE: 43
ggatatcgga tcccccagga ggtgacttta tccaagattc cttc            44

<210> SEQ ID NO 44
<211> LENGTH: 32
<212> TYPE: DNA
<213> ORGANISM: Aspergillus oryzae

<400> SEQUENCE: 44
caattgccgc gaaaaattaa attgaatcta tg                         32

<210> SEQ ID NO 45
<211> LENGTH: 28
<212> TYPE: DNA
<213> ORGANISM: Aspergillus oryzae

<400> SEQUENCE: 45
gtagtggtgg atacgtactc cttttatg                              28
```

<210> SEQ ID NO 46
<211> LENGTH: 44
<212> TYPE: DNA
<213> ORGANISM: Aspergillus oryzae

<400> SEQUENCE: 46
tcgagctcgg taccctttcag gtcacgttct aagcttatca gctg            44

<210> SEQ ID NO 47
<211> LENGTH: 40
<212> TYPE: DNA
<213> ORGANISM: Aspergillus oryzae

<400> SEQUENCE: 47
cgtatccacc actaccacta tagggcgaat tgggcccgac                   40

<210> SEQ ID NO 48
<211> LENGTH: 40
<212> TYPE: DNA
<213> ORGANISM: Aspergillus oryzae

<400> SEQUENCE: 48
gttcaaggca gacattttga cgagctgcgg aattggtcag                   40

<210> SEQ ID NO 49
<211> LENGTH: 40
<212> TYPE: DNA
<213> ORGANISM: Aspergillus oryzae

<400> SEQUENCE: 49
ccaccactac cccgggaagc gtaacaggat agcctagacc                   40

<210> SEQ ID NO 50
<211> LENGTH: 42
<212> TYPE: DNA
<213> ORGANISM: Aspergillus oryzae

<400> SEQUENCE: 50
ctgcaggatg attagagtaa cccattcccg gttctctagc tg                42

<210> SEQ ID NO 51
<211> LENGTH: 33
<212> TYPE: DNA
<213> ORGANISM: Acremonium cellulolyticus

<400> SEQUENCE: 51
atgtctgcct tgaactcttt caatatgtac aag                          33

<210> SEQ ID NO 52
<211> LENGTH: 46
<212> TYPE: DNA
<213> ORGANISM: Acremonium cellulolyticus

<400> SEQUENCE: 52
atcctgttac gcttcctaca aacattgaga gtagtaaggg ttcacg            46

<210> SEQ ID NO 53
<211> LENGTH: 26
<212> TYPE: DNA
<213> ORGANISM: Aspergillus oryzae

<400> SEQUENCE: 53

```
ctaatcatcc tgcagctccg tcattg                                        26

<210> SEQ ID NO 54
<211> LENGTH: 42
<212> TYPE: DNA
<213> ORGANISM: Aspergillus oryzae

<400> SEQUENCE: 54
ttttcgcggc aattggcaag ctcgagcatc caactaaact ag                      42
```

The invention claimed is:

1. A combination of a base sequence for protein expression comprising:
   a gene encoding protein;
   a promoter of the gene, the promoter being linked upstream of the gene; and
   a cis element whose activity is improved by an artificial transcription factor, the cis element being linked upstream of the promoter, and
   a base sequence for artificial transcription factor expression comprising: a gene encoding the artificial transcription factor; and a promoter of the gene, the promoter being linked upstream of the gene,
   wherein the cis element is represented by SEQ ID NO: 1, and
   wherein the artificial transcription factor comprises a DNA binding domain comprising a polynucleotide sequence of upstream 1 to 118 aa of a transcription factor KojR and an active domain comprising a base polynucleotide sequence of downstream 150 to 604 aa of a transcription factor AmyR, and the active domain is linked downstream of the DNA binding domain, and is represented by SEQ ID NO: 2.

2. The base sequence for protein expression according to claim 1, wherein the cis element(s) is (are) linked upstream of the promoter of the gene encoding the protein at any number in a range of 1 copy to 10 copies.

3. An expression vector including a combination of a base sequence for protein expression, the base sequence for protein expression comprising:
   a gene encoding protein;
   a promoter of the gene, the promoter being linked upstream of the gene; and
   a cis element whose activity is improved by an artificial transcription factor, the cis element being linked upstream of the promoter, and
   a base sequence for artificial transcription factor expression comprising: a gene encoding the artificial transcription factor; and a promoter of the gene, the promoter being linked upstream of the gene,
   wherein the cis element is represented by SEQ ID NO: 1, and
   wherein the artificial transcription factor comprises a DNA binding domain comprising a polynucleotide sequence of upstream 1 to 118 aa of a transcription factor KojR and an active domain comprising a polynucleotide sequence of downstream 150 to 604 aa of a transcription factor AmyR, and the active domain is linked downstream of the DNA binding domain, and is represented by SEQ ID NO: 2.

4. The expression vector according to claim 3, wherein in the base sequence for protein expression, the cis element(s) is (are) linked upstream of the promoter of the gene encoding the protein at any number in a range of 1 copy to 10 copies.

5. A transformant including a combination of a base sequence for protein expression, the base sequence for protein expression comprising:
   a gene encoding protein;
   a promoter of the gene, the promoter being linked upstream of the gene; and
   a cis element whose activity is improved by an artificial transcription factor, the cis element being linked upstream of the promoter, and
   a base sequence for artificial transcription factor expression comprising: a gene encoding the artificial transcription factor; and a promoter of the gene, the promoter being linked upstream of the gene,
   wherein the cis element is represented by SEQ ID NO: 1, and
   wherein the artificial transcription factor comprises a DNA binding domain comprising a polynucleotide of upstream 1 to 118 aa of a transcription factor KojR and an active domain comprising a polynucleotide sequence of downstream 150 to 604 aa of a transcription factor AmyR, and the active domain is linked downstream of the DNA binding domain, and is represented by SEQ ID NO: 2.

6. The transformant according to claim 5, wherein in the base sequence for protein expression, the cis element(s) is (are) linked upstream of the promoter of the gene encoding the protein at any number in a range of 1 copy to 10 copies.

7. The transformant according to claim 5, wherein said transformant is derived from koji mold used as a host cell.

8. The transformant according to claim 7, wherein the koji mold is an Aspergillus oryzae HO2 strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NITE BP-01750).

9. The transformant according to claim 7, wherein the koji mold is an Aspergillus oryzae HO4 strain (National Institute of Technology and Evaluation, Patent Microorganisms Depositary, #122, 2-5-8 Kazusakamatari, Kisarazu-shi, Chiba, Japan, Deposition Date: Dec. 9, 2014, Deposition No.: NITE BP-01980).

10. A method for producing protein, comprising
    culturing a transformant including a combination of a base sequence for protein expression which comprises:
    a gene encoding the protein; a promoter of the gene, the promoter being linked upstream of the gene; and a cis element whose activity is improved by an artificial transcription factor, the cis element being linked upstream of the promoter, wherein the cis element is represented by SEQ ID NO: 1, and a base sequence for artificial transcription factor expression comprising: a gene encoding the artificial transcription factor; and a promoter of the gene, the promoter being linked upstream of the gene, and recovering the protein encoded by the gene overexpressed by the base sequence for protein expression, from a medium or inside of the transformant after the culture, wherein the artificial transcription factor comprises a DNA binding domain comprising a polynucleotide sequence of upstream 1 to 118 aa of a transcription factor KojR and an active domain comprising a polynucleotide sequence of downstream 150 to 604 aa of a transcription factor AmyR, and the active domain is linked downstream of the DNA binding domain, and is represented by SEQ ID NO: 2.

11. The method for producing protein according to claim 10, wherein in the base sequence for protein expression, the cis element(s) is (are) linked upstream of the promoter of the gene encoding the protein at any number in a range of 1 copy to 10 copies.

* * * * *